United States Patent [19]

Lewis et al.

[11] 4,202,983

[45] May 13, 1980

[54] 11-(LOWER-ALKOXY- AND LOWER-ALKYLTHIO-3-OXO-LOWER-ALKYL)-HEXAHYDRO-2,6-M ETHANO-BENZAZOCINES

[75] Inventors: Thomas R. Lewis, Bethlehem; William F. Michne, Poestenkill, both of N.Y.

[73] Assignee: Sterling Drug Inc., New York, N.Y.

[21] Appl. No.: 23,613

[22] Filed: Mar. 26, 1979

Related U.S. Application Data

[63] Continuation-in-part of Ser. No. 886,782, Mar. 15, 1978, abandoned.

[51] Int. Cl.[2] .......... C07D 221/26

[52] U.S. Cl. .......... 546/97; 424/267; 546/43; 546/74

[58] Field of Search .......... 546/97, 74

[56] References Cited

U.S. PATENT DOCUMENTS

| | | | |
|---|---|---|---|
| 3,250,678 | 5/1966 | Archer | 424/267 |
| 3,733,330 | 5/1973 | Schubert et al. | 546/97 |
| 3,776,914 | 12/1973 | Atsumi | 546/97 |
| 3,932,422 | 1/1976 | Michne | 546/97 |

*Primary Examiner*—John D. Randolph

*Assistant Examiner*—Richard A. Schwartz

*Attorney, Agent, or Firm*—William G. Webb; B. Woodrow Wyatt

[57] ABSTRACT

3-$R_1$-6(eq)-$R_4$-7-$R_2''$-8-$R_2$-9-$R_2'$-10-$R_2'''$-11(ax)-$R_3$-11(eq)-[$CH_2CH_2CO(CH_2)_n$-X-Alk]-1,2,3,4,5,6-hexahydro-2,6-methano-3-benzazocines, useful as analgesics, are prepared by heating, with formic acid in an organic solvent or with certain ammonium formates, a lower-alkyl 1-$R_1$-3-[Alk-X-$(CH_2)_n$-CO]-4a$\alpha$-$R_3$-5$\alpha$-$R_4$-6-$R_2''$-7-$R_2$-8-$R_2'$-9-$R_2'''$-1,2,3,4,4a,5,10,10a-octahydro-2,5-methanobenzo[g]quinoline-3-carboxylate.

8 Claims, No Drawings

11-(LOWER-ALKOXY- AND LOWER-ALKYLTHIO-3-OXO-LOWER-ALKYL)-HEXAHYDRO-2,6-M ETHANO-BENZAZOCINES

RELATED APPLICATIONS

This is a continuation-in-part of our prior, copending application Ser. No. 886,782, filed Mar. 15, 1978, now abandoned, Mar. 26, 1979.

BACKGROUND OF THE INVENTION (a) Field of the Invention

This invention relates to 11-(lower-alkoxy- and lower-alkylthio-3-oxo-lower-alkyl)-hexahydro-2,6-methano-3-benzazocines, useful as analgesics.

(b) Prior Art

Michne U.S. Pat. No. 3,932,422, patented Jan. 13, 1976, describes certain 1,2,3,4,5,6-hexahydro-2,6-methano-3-benzazocines having 11(eq)-alkyl side chains bearing ketone or carbinol functions; and other art, for example Archer U.S. Pat. No. 3,250,678, patented May 10, 1966, describes 1,2,3,4,5,6-hexahydro-2,6-methano-3-benzazocines having an unsubstituted lower-alkyl group at the 11-position, for example methyl or ethyl. However, 1,2,3,4,5,6-hexahydro-2,6-methano-3-benzazocines having an 11-alkyl side chain substituted with other functional groups, such as oxygen or sulfur interrupted lower-alkyl side chains, are unknown in the prior art.

SUMMARY OF THE INVENTION

In a composition of matter aspect, this invention relates to certain 3-$R_1$-6(eq)-$R_4$-7-$R_2''$-8-$R_2$-9-$R_2'$-10-$R_2'''$-11(ax)-$R_3$-11(eq)-[$CH_2CH_2CO(CH_2)_n$-X-Alk]-1,2,3,4,5,6-hexahydro-2,6-methano-3-benzazocines, useful as analgesic agents.

DETAILED DESCRIPTION INCLUSIVE OF THE PREFERRED EMBODIMENTS

More specifically, this invention provides valuable compounds having the formula:

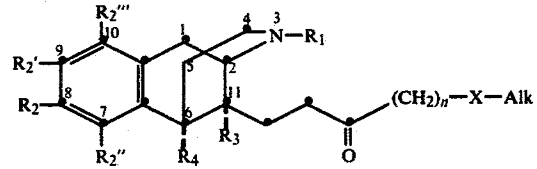

and chemically designated 3-$R_1$-6(eq)-$R_4$-7-$R_2''$-8-$R_2$-9-$R_2'$-10-$R_2'''$-11(ax)-$R_3$-11(eq)-[$CH_2CH_2CO(CH_2)_n$-X-Alk]-1,2,3,4,5,6-hexahydro-2,6-methano-3-benzazocines, and where $R_1$ is hydrogen, lower-alkyl, cycloalkyl-lower-alkyl, phenyl-lower-alkyl, lower-alkenyl or lower-alkynyl; $R_2$, $R_2'$, $R_2''$ and $R_2'''$ are each hydrogen, or three of them are hydrogen and the fourth is hydroxy, methoxymethoxy or lower-alkoxy; $R_3$ and $R_4$ are each hydrogen or lower-alkyl, or $R_3$ and $R_4$ together are divalent lower-alkylene, —$(CH_2)_m$—, where m is one of the integers 3 and 4; n is one of the integers 2–4; X is oxygen or sulfur (—O— or —S—); and Alk is lower-alkyl.

As used herein, the terms lower-alkyl or lower-alkoxy mean saturated, acyclic groups which may be straight or branched containing from one to about seven carbon atoms as exemplified by methyl, ethyl, propyl, isopropyl, butyl, methoxy, ethoxy, propoxy, isopropoxy or sec-butoxy.

As used herein, the terms lower-alkenyl and lower-alkynyl represent monovalent groups of from three to seven carbon atoms containing one double or triple bond as illustrated, for example, by 1-propenyl, 2-butenyl, 4-pentenyl, 3-methyl-2-butenyl, 1-methyl-2-propenyl, 2-methyl-2-propenyl, 2-propynyl, 2-butynyl, 4-pentynyl, 2-hexynyl and the like.

As used herein, the term cycloalkyl means saturated carbocyclic groups containing from three to seven ring carbon atoms as illustrated, for example, by cyclopropyl, cyclobutyl, cyclopentyl, cyclohexyl, 2-methylcyclobutyl, 4-ethylcyclohexyl and the like.

The compounds of Formula I are prepared by heating, with formic acid in an organic solvent, for example toluene, xylene or mesitylene, at a temperature from 100°–150° C. or with a benzyl-di-lower-alkylammonium formate or a tri-lower-alkylammonium formate at a temperature from 120°–150° C., a lower-alkyl 1-$R_1$-3-[Alk-X-$(CH_2)_n$CO]-4aα-$R_3$-5α-$R_4$-6-$R_2''$-7-$R_2$-8-$R_2'$-9-$R_2'''$-1,2,3,4,4a,5,10,10a-octahydro-2,5-methanobenzo[g]-quinoline-3-carboxylate having the formula:

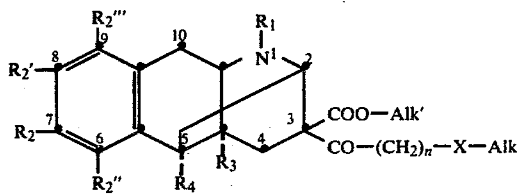

where $R_1$, $R_2$, $R_2'$, $R_2''$, R''', $R_3$, $R_4$, n, X and Alk have the meanings given above, and Alk' is lower-alkyl.

The compounds of Formula I where one of $R_2$, $R_2'$, $R_2''$ and $R_2'''$ is hydroxy are preferably prepared from the compounds of Formula II where the corresponding group is methoxymethoxy ($CH_3OCH_2O$), which group is normally cleaved to the hydroxy group under the acid conditions present during the heating of the compounds of formula II in formic acid or formate solution as described above, but in any event the group can be readily cleaved in the products of Formula I using dilute mineral acid.

The compounds of formulas I or II where one of $R_2$, $R_2'$, $R_2''$ and $R_2'''$ is methoxymethoxy are prepared by reaction of the corresponding compounds where the subject group is hydroxy with dimethoxymethane in the presence of a catalytic amount of a strong acid and in an inert organic solvent. The reaction is carried out by refluxing a solution of the reactants in the chosen solvent, for example chloroform, methylene dichloride, ethylene dichloride and the like, under a Soxhlet extractor containing molecular sieves having a pore size sufficient to trap and hold molecules of methanol.

In this way the methanol produced in the reversible reaction is removed from the reaction mixture as it is formed, and the reaction proceeds to completion. It has been found that 4A molecular sieves have a porosity of the proper size for this purpose.

The compounds of formula I where one of $R_2$, $R_2'$, $R_2''$ and $R_2'''$ is methoxymethoxy are particularly useful as intermediates for preparing the corresponding compounds where the subject group is hydroxy and which contain acid sensitive groups elsewhere in the molecule, for example compounds where $R_1$ is cycloalkyl-loweralkyl where cycloalkyl is cyclopropyl, since as indicated above the methoxymethoxy group is readily cleaved under mild acid conditions.

The compounds of formula I where $R_1$ is benzyl can be catalytically debenzylated to give the corresponding compounds where $R_1$ is hydrogen. The latter can then be realkylated, as described below, with an appropriate alkylating agent to give other different compounds where $R_1$ has the meanings, other than hydrogen, given above. Reduction is carried out in an inert organic solvent, for example ethanol, isopropanol, and the like, and at pressures from 40 to 100 p.s.i.g. A preferred catalyst is palladium-on-charcoal. The alkylation of the compounds of formula I where $R_1$ is hydrogen is carried out in an inert organic solvent, for example acetone, ethanol or DMF, and in the presence of an acid-acceptor, for example alkali metal carbonates or bicarbonates.

The compounds of formula I where $R_1$ is lower-alkenyl, lower-alkynyl, cycloalkyl-lower-alkyl or phenyl-lower-alkyl (e.g. phenylethyl) are advantageously prepared from the corresponding compounds where $R_1$ is hydrogen by reaction of the latter with an appropriate lower-alkenyl halide, lower-alkynyl halide, cycloalkyl-lower-alkyl halide or phenyl-lower-alkyl halide, as the case may be, in an inert organic solvent, for example a lower-alkanol, acetone or dimethylformamide (hereinafter designated DMF), in the presence of an acid-acceptor, for example an alkali metal carbonate or bicarbonate. A preferred solvent is DMF.

An alternative method for preparing the compounds of formula I, where one of $R_2$, $R_2'$, $R_2''$ and $R_2'''$ is either hydrogen or hydroxy; n is the integer 3; and X is S, comprises reacting a compound having the formula:

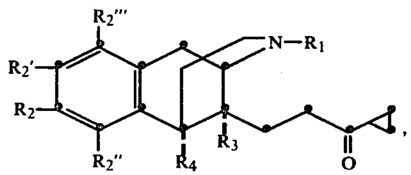

where $R_2$, $R_2'$, $R_2''$ and $R_2'''$ have the particular meanings given above, and $R_1$, $R_3$ and $R_4$ have the meanings previously indicated, with an alkali metal lower-alkanethiol, Alk-S-M, where M is an alkali metal cation, and Alk has the meaning given above. The reaction is carried out in an inert organic solvent, for example dimethylformamide (DMF), preferably at the reflux temperature thereof. As will be seen the reaction involves ring opening of the cyclopropyl ring by the lower-alkylthio anion which will also cleave any ether groups present in the molecule, i.e. one of $R_2$, $R_2'$, $R_2''$ and $R_2'''$ is lower-alkoxy. Thus when the starting material of Formula III contains an ether function, at least two molar equivalents of the alkali metal lower-alkanethiol are required.

The compounds of Formula III are disclosed in Michne, U.S. patent application Ser. No. 877,166, filed Feb. 13, 1978, and continuation-in-part thereof Ser. No. 9,594, filed Feb. 5, 1979, the disclosures of which are incorporated herein by reference.

The compounds of Formula II and the method for their preparation are disclosed in our U.S. Pat. No. 4,119,628, patented Oct. 10, 1978 and continuation-in-part thereof, Ser. No. 878,308, filed Feb. 16, 1978, now U.S. Pat. No. 4,148,794, patented Apr. 10, 1979 the disclosures of which are incorporated herein by reference. This method comprises reacting a lower-alkyl 1-$R_1$-4a$\alpha$-$R_3$-5$\alpha$-$R_4$-6-$R_2''$-7-$R_2$-8-$R_2'$-9-$R_2'''$-1,2,3,4,4a,5,10,10a-octahydro-2,5-methanobenzo[g-]quinoline-3-carboxylate having the formula:

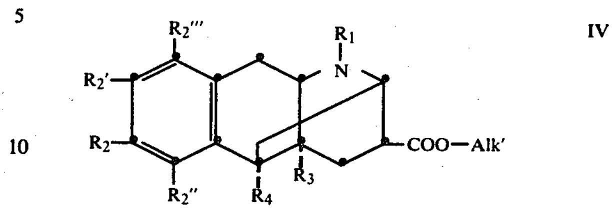

with an alkali metal amide, and reacting the resulting alkali metal salt with an appropriate acid halide, Alk-X-$(CH_2)_n$-CO-Hal, where Hal is halogen.

The compounds of Formula IV and the method for their preparation are disclosed in Michne U.S. Pat. No. 4,100,164, patented July 11, 1978, the disclosure of which is also incorporated herein by reference.

Due to the presence of a basic amino grouping, the free base form represented by Formula I above reacts with organic and inorganic acids to form acid-addition salts. The acid-addition salt forms are prepared from any organic or inorganic acid. They are obtained in conventional fashion, for instance either by direct mixing of the base with the acid or, when this is not appropriate, by dissolving either or both of the base and the acid separately in water or an organic solvent and mixing the two solutions, or by dissolving both the base and the acid together in a solvent. The resulting acid-addition salt is isolated by filtration, if it is insoluble in the reaction medium, or by evaporation of the reaction medium to leave the acid-addition salt as a residue. The acid moieties or anions in these salt forms are in themselves neither novel nor critical and therefore can be any acid anion or acid-like substance capable of salt formation with the base.

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicyclic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacetic acid, barbituric acid, sulfamic acid, methanesulfonic acid, ethanesulfonic acid, isethionic acid, benzenesulfonic acid, p-toluenesulfonic acid, butylarsonic acid, methanephosphonic acid, acidic resins, hydrofluoric acid, hydrochloric acid, hydrobromic acid, hydriodic acid, perchloric acid, nitric acid, sulfuric acid, phosphoric acid, arsenic acid, and the like.

All of the acid-addition salts are useful as sources of the free base forms, by reaction with an inorganic base. It will thus be appreciated that if one or more of the characteristics, such as solubility, molecular weight, physical appearance, toxicity, or the like of a given base or acid-addition salt thereof render that form unsuitable for the purpose at hand, it can be readily converted to another, more suitable form. For pharmaceutical purposes, acid-addition salts of relatively non-toxic, pharmaceutically-acceptable acids, for example hydrochloric acid, lactic acid, tartaric acid, and the like, are of course employed.

The compounds of this invention can exist in enantiomeric forms separable into enantiomers. If desired, the isolation or the production of a particular enantiomeric form can be accomplished by application of general principles known in the prior art. In the nomenclature employed for the compounds of Formula I herein, "ax" stands for axial and "eq" for equatorial, and the configurations are given with reference to the hydroaromatic ring. Thus, the 6(eq), 11(ax) compounds of Formula I are in the cis configuration, whereas the 6(eq), 11(eq) compounds are in the trans configuration.

In the nomenclature employed for the compounds of Formulas II and III, again configurations are given with reference to the hydroaromatic ring, and the designation "$\beta$" indicates the cis configuration relative to the 2,5-methano bridge of the compounds of Formula II. Conversely, the designation "$\alpha$" indicates the trans configuration relative to the same groups.

In standard pharmacological test procedures, the compounds of Formula I and the acid-addition salts thereof have been found useful as depressants of the central nervous system, and more particularly have been found useful as analgesics and as antagonists of strong analgesics such as phenazocine, meperidine and morphine.

The compounds of Formula I can be administered in the same manner as known analgesics and antagonists of strong analgesics, i.e. parenterally or orally in any of the conventional pharmaceutical forms, as for instance solutions, suspensions, tablets, capsules, and the like.

As described above and as will be seen hereinbelow, many of the species of Formula I are readily interconvertible by simple and well-known reactions such as ether cleavage, etherification, and the like, so that they are also useful as intermediates for each other.

The useful properties of the compounds of this invention were demonstrated by standard pharmacological procedures readily carried out by technicians having ordinary skill in pharmacological test procedures, so that the actual determination of numerical biological data definitive for a particular test compound can be ascertained without the need for any extensive experimentation.

The test procedures used to determine analgesic and analgesic antagonist activities of the compounds of the invention have been described in detail in the prior art and are as follows: The acetylcholine-induced abdominal constriction test, which is a primary analgesic screening test designed to measure the ability of a test agent to suppress acetylcholine-induced abdominal constriction in mice, described by Collier et al., Brit. J. Pharmacol. Chemotherap. 32, 295 (1968); a modification of the anti-bradykinin test, which is also a primary analgesic screening procedure, described by Berkowitz et al., J. Pharmacol. Exp. Therap. 177, 500–508 (1971), Blane et al., J. Pharm. Pharmacol. 19, 367–373 (1967), Botha et al., Eur. J. Pharmacol. 6, 312–321 (1969) and Deffenu et al., J. Pharm. Pharmacol 18, 135 (1966); the phenyl-p-qunione-induced writhing test, also a primary analgesic screening test, designed to measure the ability of a test agent to prevent phenyl-p-quinone-induced writhing in mice, described by Pearl and Harris, J. Pharmacol. Exptl. Therap. 154, 319–323 (1966); the rat tail flick radiant thermal heat analgesic (agonist) test described by D'Amour and Smith, J. Pharmacol. Exptl. Therap. 72, 74 (1941) as modified by Bass and Vander-Brook, J. Am. Pharm. Assoc. Sci. Ed. 41, 569 (1956); and the narcotic antagonist test using phenazocine or morphine, which is designed to measure the ability of a test agent to antagonize the effect of phenazocine or morphine in the above-indicated rat tail flick response test, described by Harris and Pierson, J. Pharmacol. Exptl. Therap. 143, 141 (1964).

The structures of the compound of this invention were established by the modes of synthesis, by elementary analyses and by ultraviolet, infrared and nuclear magnetic resonance spectra. The course of reactions and homogenity of the products were ascertained by thin layer chromatography.

The manner and process of making and using the invention, and the best mode contemplated by the inventors of carrying out this invention, will now be described so as to enable any person skilled in the art to which it pertains to make and use the same. The melting points are uncorrected.

EXAMPLE 1

A solution of 1.5 g. (0.0033 mole) of ethyl 1,4a$\alpha$,5$\alpha$-trimethyl-3-($\gamma$-methylmercaptobutyryl)-7-methoxy-1,2,3,4,4a,5,10,10a-octahydro-2,5-methanobenzo[g-]quinoline-3-carboxylate in 10 ml. of trimethylammonium formate was heated under reflux for fifteen minutes, then cooled, treated with ice and rendered strongly basic by the addition of aqueous sodium hydroxide. The mixture was extracted twice with diethyl ether, the ether extracts washed with brine, dried over magnesium sulfate and evaporated to dryness to give 1.1 g. of an oil which was dissolved in acetone and treated with 0.31 g. of methanesulfonic acid in acetone. The material which separated was collected and dried to give 1.1 g. of 3,6(eq),11(ax)-trimethyl-8-methoxy-11(eq)-(6-methylmercapto-3-oxohexyl)-1,2,3,4,5,6-hexahydro-2,6-methano-3-benzazocine methanesulfonate, m.p. 140°–143° C.

EXAMPLE 2

A solution of 8.8 g. (0.018 mole) of 3,6(eq),11(ax)-trimethyl-8-methoxy-11(eq)-(6-methylmercapto-3-oxohexyl)-1,2,3,4,5,6-hexahydro-2,6-methano-3-benzazocine methanesulfonate and 1.5 g. (0.004 mole) of the corresponding free base in 45 ml. of 48% aqueous hydrobromic acid was heated at 85° C. for about three and one-half hours under a nitrogen atmosphere. The mixture was then taken to dryness in vacuo, and the mixture was suspended in a mixture of ice and saturated sodium bicarbonate and then extracted with methylene dichloride. The combined extracts, on drying and evaporation to dryness, afforded 4.5 g. of a residual oil, which was extracted two times with boiling hexane. The residual insoluble material slowly crystallized and was collected to give 2.4 g. of material which was dissolved in methanol and chromatographed on a 200 g. silica column and eluted with a 50:50:3 hexane:diethyl ether:isopropyl alcohol solution. The first 200 ml. of eluate was discarded, and the next 750 ml. was collected and evaporated to dryness to give material having m.p. 88.5°–92° C. The latter was purified once again by streaking on silica gel plates and developing with a 60:40:3 hexane:diethyl ether:isopropyl alcohol solution. Recovery of the main product from the silica gel plate afforded 2.9 g. of material having m.p. 83°–91° C. Conversion of the latter to the ethanesulfonate salt afforded 2.8 g. of 3,6(eq),11(ax)-trimethyl-8-hydroxy-11(eq)-(6-methylmercapto-3-oxohexyl)-1,2,3,4,5,6-hexahydro- 2,6-methano-3-benzazocine ethanesulfonate, m.p. 169°–172° C.

EXAMPLE 3

To a mixture of 6.8 g. (0.02 mole) of 3,6(eq),11(ax)-trimethyl-8-methoxy-11(eq)-(3-cyclopropyl-3-oxo-propyl)-1,2,3,4,5,6-hexahydro-2,6-methano-3-benzazocine, 100 ml. of DMF and 4.8 g. (0.10 mole) of a 50% suspension of sodium hydride in mineral oil was added 10.8 ml. (0.10 mole) of propanethiol. When hydrogen evolution had ceased, the mixture was heated under reflux for three hours, then cooled and poured into one liter of dilute aqueous methanesulfonic acid. Washing the aqueous solution with diethyl ether, then basifying and extraction once again with diethyl ether and evaporation of the extracts to dryness afforded 7.2 g. of an oil. The latter was dissolved in absolute ethanol, and the solution was treated with a molar excess of sulfuric acid and diluted with diethyl ether. The crystalline material which separated was collected and recrystallized several times from ethanol/diethyl ether to give 1.8 g. of 3,6(eq),11(ax)-trimethyl-8-hydroxy-11(eq)-(6-propylmercapto-3-oxohexyl)-1,2,3,4,5,6-hexahydro-2,6-methano-3-benzazocine sulfate, m.p. 198°–202° C.

EXAMPLE 4

Following a procedure similar to that described in Examples 1 or 2, it is contemplated that reaction of ethyl 5α-ethyl-1,2,3,4,4a,5,10,10a-octahydro-2,5-methanobenzo[g]quinoline-3-carboxylate with lithium diisopropylamide, followed by reaction of the resulting lithium salt with γ-methylmercaptobutyryl chloride and treatment of the resulting product with dilute mineral acid affords ethyl 5α-ethyl-3-(γ-methylmercaptobutyryl)-1,2,3,4,4a,5,10,10a-octahydro-2,5-methanobenzo[g]quinoline-3-carboxylate, which, on heating with trimethylammonium formate, affords 6(eq)-ethyl-11(eq)-(6-methylmercapto-3-oxohexyl)-1,2,3,4,5,6-hexahydro-2,6-methano-3-benzazocine.

The latter, on reaction with a molar equivalent amount of cyclopropylmethyl bromide; 2-phenylethyl bromide; allyl bromide; or propargyl bromide in the presence of a molar equivalent amount of sodium carbonate in DMF affords, respectively, 3-cyclopropylmethyl-6(eq)-ethyl-11(eq)-(6-methylmercapto-3-oxohexyl)-1,2,3,4,5,6,-hexahydro-2,6-methano-3-benzazocine; 3-(2-phenylethyl)-6(eq)-ethyl-11(eq)-(6-methylmercapto-3-oxohexyl)-1,2,3,4,5,6-hexahydro-2,6-methano-3-benzazocine; 3-(3-propen-1-yl)-6(eq)-ethyl-11(eq)-(6-methylmercapto-3-oxohexyl)-1,2,3,4,5,6-hexahydro-2,6-methano-3-benzazocine; and 3-(3-propyn-1-yl)-6(eq)-ethyl-11(eq)-(6-methylmercapto-3-oxohexyl)-1,2,3,4,5,6-hexahydro-2,6-methano-3-benzazocine.

EXAMPLE 5

Following a procedure similar to that described in Examples 1, 2 or 4, it is contemplated that reaction of ethyl 1-methyl-7-methoxy-4aα,5α-tetramethylene-1,2,3,4,4a,5, 10,10a-octahydro-2,5-methanobenzo[g-]quinoline-3-carboxylate with aqueous hydrobromic acid affords ethyl 1-methyl-7-hydroxy-4aα,5α-tetramethylene-1,2,3,4,4a,5,10,10a-octahydro-2,5-methanobenzo[g]quinoline-3-carboxylate, which on reaction with dimethoxymethane in methylene dichloride under a Soxhlet extractor containing 4A molecular sieves affords ethyl 1-methyl-7-methoxymethoxy-4aα,-5α-tetramethylene-1,2,3,4,4a,5,10,10a-octahydro-2,5-methanobenzo[g]quinoline-3-carboxylate which, on reaction with lithium diisopropylamide, followed by reaction of the resulting lithium salt with γ-methylmercaptobutyryl chloride and treatment of the resulting product with dilute mineral acid affords ethyl 1-methyl-3-(γ-methylmercaptobutyryl)-7-hydroxy-4aα,5α-tetramethylene-1,2,3,4,4a,5,10,10a-octahydro-2,5-methanobenzo[g]quinoline-3-carboxylate which, on heating with trimethylammonium formate, affords 3-methyl-8-hydroxy-11(eq)-(6-methylmercapto-3-oxohexyl)-6(eq),11(ax)-tetramethylene-1,2,3,4,5,6-hexahydro-2,6-methano-3-benzazocine.

EXAMPLE 6

Following a procedure similar to that described in Examples 1, 2 or 4, it is contemplated that reaction of ethyl 1,4aα,5α-trimethyl-7-hydroxy-1,2,3,4,4a,5,10,10a-octahydro-2,5-methanobenzo[g]quinoline-3-carboxylate with dimethoxymethane in methylene dichloride under a Soxhlet extractor containing 4A molecular sieves affords ethyl 1,4aα,5α-trimethyl-7-methoxymethoxy-1,2,3,4,4a,5,10,10a-octahydro-2,5-methanobenzo[g]-quinoline-3-carboxylate which, on reaction with lithium diisopropylamide, followed by reaction of the resulting lithium salt with γ-methoxybutyryl chloride and treatment of the resulting product with dilute mineral acid affords ethyl 1,4aα,5α-trimethyl-3-(γ-methoxybutyryl)-7-hydroxy-1,2,3,4,4a,5,10,10a-octahydro-2,5-methanobenzo[g]quinoline-3-carboxylate which, on heating with trimethylammonium formate, affords 3,6(eq),11(ax)-trimethyl-8-hydroxy-11(eq)-(6-methoxy-3-oxohexyl)-1,2,3,4,5,6-hexahydro-2,6-methano-3-benzazocine.

EXAMPLE 7

Following a procedure similar to that described above in Examples 1, 2 or 4, it is contemplated that the following compounds of Formula I can also be prepared:

A. Reaction of ethyl 1,5α-dimethyl-6-methoxy-1,2,3,4,4a,5,10,10a-octahydro-2,5-methanobenzo[g-]quinoline-3-carboxylate with lithium diisopropylamide followed by reaction of the resulting lithium salt with β-methylmercaptopropionyl chloride affords ethyl 1,5α-dimethyl-3-(β-methylmercaptopropionyl)-6-methoxy-1,2,3,4,4a,5,10,10a-octahydro-2,5-methanobenzo[g]-quinoline-3-carboxylate which, on heating with trimethylammonium formate, affords 3,6(eq)-dimethyl-7-methoxy-11(eq)-(5-methylmercapto-3-oxopentyl)-1,2,3,4,5,6-hexahydro-2,6-methano-3-benzazocine.

B. Reaction of ethyl 1,4aα-dimethyl-8-methoxy-1,2,3,4,4a,5,10,10a-octahydro-2,5-methanobenzo[g-]quinoline-3-carboxylate with lithium diisopropylamide followed by reaction of the resulting lithium salt with δ-ethoxypentanoyl chloride affords 1,4aα-dimethyl-3-(δ-ethoxypentanoyl)-8-methoxy-1,2,3,4,4a,5,10,10a-octahydro-2,5-methanobenzo[g]quinoline-3-carboxylate which, on heating with trimethylammonium formate, affords 3,11(ax)-dimethyl-9-methoxy-11(eq)-(7-ethoxy-3-oxoheptyl)-1,2,3,4,5,6-hexahydro-2,6-methano-3-benzazocine.

C. Reaction of ethyl 1,4aα,5α-trimethyl-9-methoxy-1,2,3,4,4a,5,10,10a-octahydro-2,5-methanobenzo[g-]quinoline-3-carboxylate with lithium diisopropylamide followed by reaction of the resulting lithium salt with γ-methylmercaptobutyryl chloride affords ethyl 1,4aα,-5α-trimethyl-3-(γ-(methylmercaptobutyryl)-9- methoxy-1,2,3,4,4a,5,10,10a-octahydro-2,5-methanobenzo[g]quinoline-3-carboxylate which, on heating with trimethylammonium formate, affords 3,6(eq),11(ax)-trimethyl-10-methoxy-11(eq)-(6-methylmercapto-3-oxohexyl)-1,2,3,4,5,6-hexahydro-2,6-methano-3-benzazocine.

D. Reaction of ethyl 1-methyl-4a$\alpha$,5a-trimethylene-7-methoxy-1,2,3,4,4a,5,10,10a-octahydro-2,5-methanobenzo[g]-quinoline-3-carboxylate with lithium diisopropylamide followed by reaction of the resulting lithium salt with $\beta$-methylmercaptopropionyl chloride affords ethyl 1-methyl-4a$\alpha$,5$\alpha$-trimethylene-3-($\beta$-methylmercaptopropionyl)-7-methoxy-1,2,3,4,4a,5,10,-10a-octahydro-2,5-methanobenzo[g]quinoline-3-carboxylate which, on heating with trimethylammonium formate, affords 3-methyl-6(eq),11(ax)-trimethylene-8-methoxy-11(eq)-(5-methylmercapto-3-oxopentyl)-1,2,3,4,5,6-hexahydro-2,6-methano-3-benzazocine.

E. Reaction of ethyl 1-methyl-4a$\alpha$,5$\alpha$-trimethylene-7-methoxy-1,2,3,4,4a,5,10,10a-octahydro-2,5-methanobenzo[g]quinoline-3-carboxylate with lithium diisopropylamide followed by reaction of the resulting lithium salt with $\beta$-methylmercaptopropionyl chloride affords ethyl 1-methyl-4a$\alpha$,5$\alpha$-tetramethylene-3-($\beta$-methylmercaptopropionyl)-7-methoxy-1,2,3,4,4a,5,10,-10a-octahydro-2,5-methanobenzo[g]quinoline-3-carboxylate which, on heating with trimethylammonium formate, affords 3-methyl-6(eq),11(ax)-tetramethylene-8-methoxy-11(eq)-(5-methylmercapto-3-oxopentyl)-1,2,3,4,5,6-hexahydro-2,6-methano-3-benzazocine.

BIOLOGICAL TEST RESULTS

The compounds of Formula I are generally active in the acetylcholine-induced abdominal constriction test (Ach), a primary analgesic screening test, and also in the rat tail flick radiant thermal heat agonist test, (T.F. Ag.) and also in the Straub tail test (Straub). Individual species have also been found inactive in the phenazocine tail flick antagonist (Phen) test thus indicating that the species are analgesics and not analgesic antagonists.

Thus the compound of Example 1 was found to have an $ED_{50}$ of 0.50 mg./kg. (s.c.) and 2.0 mg./kg. (s.c.) in the acetylcholine-induced abdominal constriction and tail flick agonist tests, respectively. The activity in the latter test was prevented by 1.0 mg./kg. (s.c.) of nalorphine. The compound was found inactive in the phenazocine antagonist test at doses of 0.1 and 0.01 mg./kg. (s.c.). The Straub tail reaction was noted in mice at a dose of 7.5 mg./kg.

The $ED_{50's}$ in the acetylcholine-induced abdominal constriction test and the anti-bradykinin test and the $AD_{50's}$ vs. phenazocine and morphine in the narcotic antagonist test of the compound of Example 2 were found to be, respectively, 0.1–1.0 mg./kg. (s.c.), 0.071 mg./kg. (s.c.), 0.0034 mg./kg. (s.c.) and 0.18 mg./kg. (s.c.). The same compound was found to be inactive in the tail flick agonist test at 120 mg./kg. (s.c.).

The compound of Example 3 was found to be essentially inactive in the acetylcholine-induced abdominal constriction test (60% inhibition/20 mg./kg.; 53%/10 mg./kg.; 40%/1 mg./kg.; and 7%/0.1 mg./kg.—all s.c.) and also in the anti-bradykinin test [0/5 protected at 1.0 and 10.0 mg./kg. (s.c.)]. The $AD_{50}$ vs. phenazocine in the tail flick antagonist test was found to be 0.046 mg./kg. (s.c.).

We claim:

1. A compound having the formula:

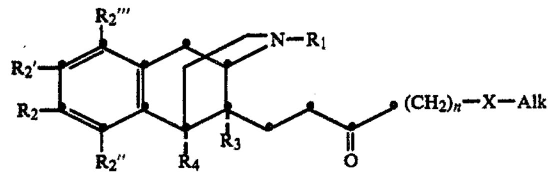

where $R_1$ is hydrogen, lower-alkyl, cycloloweralkyl-lower-alkyl, phenyl-lower-alkyl, lower-alkenyl or lower-alkynyl; $R_2$, $R_2'$, $R_2''$ and $R_2'''$ are each hydrogen, or three of them are hydrogen and the fourth is hydroxy, methoxymethoxy or lower-alkoxy; $R_3$ and $R_4$ are each hydrogen or lower-alkyl, or $R_3$ and $R_4$ together are divalent lower-alkylene, —$(CH_2)_m$—, where m is one of the integers 3 and 4; n is one of the integers from 2 to 4; X is oxygen or sulfur; and Alk is lower-alkyl; or an acid-addition salt thereof.

2. A compound according to claim 1 where $R_2$ is lower-alkoxy; $R_2'$, $R_2''$ and $R_2'''$ are each hydrogen; each of $R_3$ and $R_4$ is lower-alkyl; and X is sulfur.

3. A compound according to claim 1 where $R_2$ is hydroxy; $R_2'$, $R_2''$ and $R_2'''$ are each hydrogen; each of $R_3$ and $R_4$ is lower-alkyl; and X is sulfur.

4. A compound according to claim 1 where $R_2$ is hydroxy; $R_2'$, $R_2''$ and $R_2'''$ are each hydrogen; $R_3$ and $R_4$ together are lower-alkylene, —$(CH_2)_m$—, where m is one of the integers 3 and 4; and X is sulfur.

5. 3,6(eq),11(ax)-Trimethyl-8-methoxy-11(eq)-(6-methylmercapto-3-oxohexyl)-1,2,3,4,5,6-hexahydro-2,6-methano-3-benzazocine according to claim 2.

6. 3,6(eq),11(ax)-Trimethyl-8-hydroxy-11(eq)-(6-methylmercapto-3-oxohexyl)-1,2,3,4,5,6-hexahydro-2,6-methano-3-benzazocine according to claim 3.

7. 3,6(eq),11(ax)-Trimethyl-8-hydroxy-11(eq)-(6-propylmercapto-3-oxohexyl)-1,2,3,4,5,6-hexahydro-2,6-methano-3-benzazocine according to claim 3.

8. A compound according to claim 4 where m is the integer 4 and $R_1$ is lower-alkyl.

* * * * *

UNITED STATES PATENT AND TRADEMARK OFFICE
CERTIFICATE OF CORRECTION

PATENT NO. : 4,202,983

DATED : May 13, 1980

INVENTOR(S) : Thomas R. Lewis and William F. Michne

It is certified that error appears in the above-identified patent and that said Letters Patent are hereby corrected as shown below:

On the face page and in column 1, change "11-(LOWER-ALKOXY- AND LOWER-ALKYLTHIO-3-OXO-LOWER-ALKYL)-HEXAHYDRO-2,6-M ETHANO-BENZAZOCINES" to read --11-(LOWER-ALKOXY-AND LOWER-ALKYTHIO-3-OXO-LOWER-ALKYL)-HEXAHYDRO-2,6-METHANO-3-BENZAZOCINES--.

Column 6, line 12, change "homogenity" to read --homogeneity--.

Column 10, lines 23-24, Claim 1, change "cycloloweralkyl..." to read --cyclo-lower-alkyl-....--.

Signed and Sealed this

*Twenty-first* Day of *December 1982*

[SEAL]

*Attest:*

GERALD J. MOSSINGHOFF

*Attesting Officer* *Commissioner of Patents and Trademarks*